United States Patent
Kamen et al.

(10) Patent No.: US 10,335,238 B2
(45) Date of Patent: Jul. 2, 2019

(54) SYSTEM AND METHOD FOR NON-INVASIVELY ESTIMATING ELECTROPHYSIOLOGICAL MAPS AND MEASUREMENTS FROM CARDIO-THORACIC 3D IMAGES AND ELECTROCARDIOGRAPHY DATA

(71) Applicant: SIEMENS HEALTHCARE GMBH, Erlangen (DE)

(72) Inventors: Ali Kamen, Skillman, NJ (US); Tommaso Mansi, Plainsboro, NJ (US); Tiziano Passerini, Plainsboro, NJ (US); Bogdan Georgescu, Plainsboro, NJ (US); Saikiran Rapaka, Pennington, NJ (US); Dorin Comaniciu, Princeton Junction, NJ (US); Gabriel Haras, Mücke (DE)

(73) Assignee: Siemens Healthcare GmbH, Erlangen (DE)

( * ) Notice: Subject to any disclaimer, the term of this patent is extended or adjusted under 35 U.S.C. 154(b) by 616 days.

(21) Appl. No.: 14/670,707

(22) Filed: Mar. 27, 2015

(65) Prior Publication Data

US 2016/0283687 A1    Sep. 29, 2016

(51) Int. Cl.
| | | |
|---|---|---|
| *G06F 19/00* | (2018.01) | |
| *A61B 5/00* | (2006.01) | |
| *A61B 34/10* | (2016.01) | |
| *A61B 5/0402* | (2006.01) | |
| *A61B 5/044* | (2006.01) | |
| *G06T 19/00* | (2011.01) | |
| *G16H 50/50* | (2018.01) | |

(52) U.S. Cl.
CPC ............ *A61B 34/10* (2016.02); *A61B 5/044* (2013.01); *A61B 5/04021* (2013.01); *A61B 5/04028* (2013.01); *G06T 19/00* (2013.01); *G16H 50/50* (2018.01); *A61B 5/742* (2013.01); *A61B 2576/023* (2013.01); *G06T 2210/41* (2013.01)

(58) Field of Classification Search
None
See application file for complete search history.

(56) References Cited

U.S. PATENT DOCUMENTS

| | | |
|---|---|---|
| 7,668,354 B2 | 2/2010 | O'Donnell et al. |
| 7,916,919 B2 | 3/2011 | Zheng et al. |
| 2010/0040272 A1 | 2/2010 | Zheng et al. |
| 2012/0022843 A1 | 1/2012 | Ionasec et al. |
| 2013/0197881 A1 | 8/2013 | Mansi et al. |
| 2013/0216110 A1 | 8/2013 | Zheng et al. |
| 2013/0226542 A1 | 8/2013 | Rapaka et al. |
| 2014/0088943 A1 | 3/2014 | Trayanova et al. |
| 2014/0122048 A1 | 5/2014 | Vadakkumpadan et al. |
| 2015/0042646 A1 | 2/2015 | Comaniciu et al. |

OTHER PUBLICATIONS

Zettinig et al. Med Image Comput Assist Interv. 2013;16(Pt 1):1-8.*
Peyrat et al., "A Computational Framework for the Statistical Analysis of Cardiac Diffusion Tensors: Application to a Small Database of Canine Hearts,", IEEE TMI, 26(11): 1500-1514, 2007.
Rapaka, et al., "LBM-EP: Lattice-boltzmann method for fast cardiac electrophysiology simulation from 3d images", In: Medical Image Computing and Computer-Assisted Intervention MICCAI, 2012, pp. 33-40, vol. 7511, Springer Berlin Heidelberg.

* cited by examiner

*Primary Examiner* — Michael L Borin (57) ABSTRACT

A method and system for patient-specific simulation of cardiac electrophysiology is disclosed. A patient-specific anatomical heart model is generated from medical image data of a patient. A patient-specific cardiac electrophysiology model is generated based on simulated torso potentials and body surface potential measurements of the patient. Cardiac electrophysiology of the patient is simulated over time for the patient-specific anatomical heart model using the patient-specific electrophysiology model. One or more electrophysiology maps are generated based on the cardiac electrophysiology simulated using the patient-specific cardiac electrophysiology model.

16 Claims, 5 Drawing Sheets

SYSTEM AND METHOD FOR NON-INVASIVELY ESTIMATING ELECTROPHYSIOLOGICAL MAPS AND MEASUREMENTS FROM CARDIO-THORACIC 3D IMAGES AND ELECTROCARDIOGRAPHY DATA

BACKGROUND OF THE INVENTION

The present invention relates to estimating electrophysiological maps of a patient, and more particularly to estimating electrophysiological maps of a patient from medical image data and electrocardiography data of the patient.

Cardiac disease is the number one cause of death in the United States. More than two million Americans have been diagnosed with irregular heartbeats, which are clinically referred to as cardiac arrhythmias. On the other hand, more than five million Americans have been diagnosed with some level of deficiency to properly pump blood, which is clinically referred to as congestive heart failure. Treatment of arrhythmias is primarily based on drug therapy. However, when arrhythmias become pharmacologically resistant, radio-frequency ablation therapy becomes the treatment of choice. Deficiency in pump function due to asynchronized ventricular contraction is often corrected using cardiac resynchronization therapy (CRT). While these treatments are providing more and more effective in improving patients' lifestyle and life span, the clinical outcomes are often still not satisfactory. Cardiac ablation success rates, specifically in the longer term, are low. In fact, more than 40% of patients treated require that the cardiac ablation procedure be repeated. CRT treatment has a success rate of 2/3. One out of three patients does not respond properly to the CRT treatment. For these patients, it is suspected that patient selection, along with the optimization of the lead location and device settings in the CRT treatment, are important factors as to why the CRT treatment is not successful.

Electrocardiography (ECG) is the main method for assessing a patient's cardiac electrophysiology. However, for accurate diagnosis of the cause of an arrhythmia and planning of a cardiac ablation or CRT procedure, more information is need than the electrocardiography information provided by a 12-lead ECG only. In particular, it is of high importance to know the myocardium region that causes the arrhythmia or that maximizes resynchronization. To that end, current approaches use endocardial potential and activation time maps generated using catheter based measurements. However, a limitation of such approaches is that they are invasive and also acquired over several heart beats. As a result, identifying and analyzing the complex structure of the electrical wave during arrhythmias (e.g., atrial fibrillation, ventricular tachycardia) is impossible.

BRIEF SUMMARY OF THE INVENTION

The present invention provides a method and system for non-invasively estimating patient-specific electrophysiology maps from medical image data and electrocardiography data of a patient. Embodiments of the present invention estimate not only epicardial potentials, but also whole volume dynamic potential maps from non-invasive body surface potentials. Embodiments of the present invention also provide intrinsic properties of the patient's tissue, such as action potential duration and electrical conductivity. Embodiments of the present invention provide can be used for assessing whether a treatment, such as cardiac ablation or CRT, is appropriate for a patient and for optimizing lead locations for such as treatment.

In one embodiment of the present invention, a patient-specific anatomical heart model is generated from medical image data of a patient. Torso potentials are computed over time at locations on a torso of the patient using the patient-specific anatomical heart model, a patient-specific anatomical arrangement between the heart and torso, and a cardiac electrophysiology model with certain model parameters. The model parameters are estimated and refined to minimize an error between the computed torso potentials and body surface potential measurements acquired for the patient. At least one a visualization of patient-specific electrophysiological measurements or patient-specific electrophysiology maps is generated based on the patient-specific anatomical heart model, the patient-specific anatomical arrangement between the heart and torso, and the cardiac electrophysiology model with refined model parameters.

These and other advantages of the invention will be apparent to those of ordinary skill in the art by reference to the following detailed description and the accompanying drawings.

DETAILED DESCRIPTION

The present invention relates to non-invasive estimation of patient-specific electrophysiology maps from medical imaging data and electrocardiography data of a patient. Embodiments of the present invention are described herein to give a visual understanding of the methods for estimating patient-specific electrophysiology maps from medical imaging data and electrocardiography data of a patient. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention estimate not only epicardial potentials, but also whole volume dynamic potential maps from non-invasive body surface potentials. As a result, embodiments of the present invention provide a comprehensive view of cardiac electrophysiology throughout the entire volume and not only on the epicardial surface. Furthermore, embodiments of the present invention provide intrinsic properties of the patient's tissue, such as action potential duration and electrical conductivity, as a result of an estimation process used to map back measured torso potentials on the myocardium volume. A data-driven approach can be utilized to estimate the uncertainty of such tissue properties, which can be visualized by the user. Embodiments of the present invention also provide visualization of dynamic potential maps on the epicardium, endocardium, and any layer within the myocardium and also throughout the volume, as well as tissue diffusivity and other parameters.

According to an embodiment of the present invention, a method for simulating patient-specific cardiac electrophysiology is built upon two sets of simultaneous acquisitions, i.e., anatomical imaging and body surface potential (BSP) measurements. A detailed cardiac anatomy is obtained from the anatomical imaging. Then, contrary to methods in which the BSP collected from the body torso is back-projected on the epicardium surface obtained from the images and regularized, embodiments of the present invention utilize an inverse modeling approach based on a fast computational model of cardiac electrophysiology and potential propagation throughout the torso. The computational model is used to compute a dynamic map of simulated BSP given spatially varying electrophysiology (EP) parameters such as electrical conductivity and action potential duration. An inverse problem approach is then used to minimize the difference between the simulated BSP and the BSP measurements by estimating optimal patient-specific EP parameters. Once the EP parameters have been optimized, the patient-specific computation model can recover not only the electrophysiological map in the entire myocardium volume, including the endocardial and epicardial maps, but also additional substrate information regarding the myocardium (e.g., diffusion parameters) that can be used for diagnostic purposed.

Figure 1:
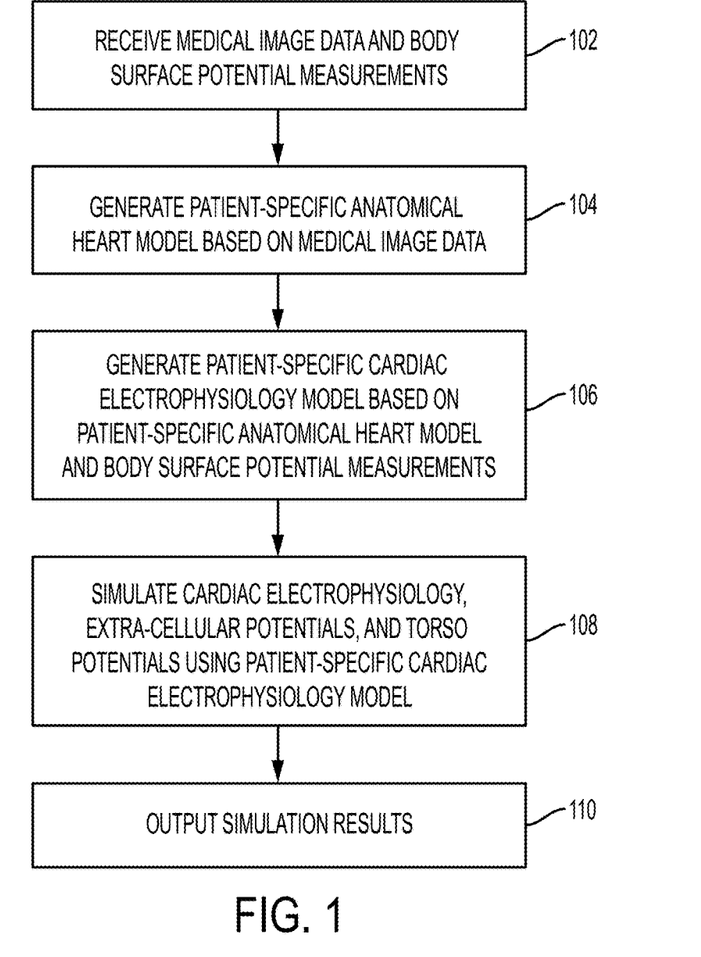
FIG. 1 illustrates a method for simulating patient-specific cardiac electrophysiology according to an embodiment of the present invention.

FIG. 1 illustrates a method for simulating patient-specific cardiac electrophysiology according to an embodiment of the present invention. The method of FIG. 1 transforms medical image data of a patient to simulate cardiac electrophysiology of the patient over a period of time and generate patient-specific electrophysiology maps for the epicardium, endocardium, and any layer of the myocardium. Referring to FIG. 1, at step 102, medical image data and body surface potential (BSP) measurements of a patient are received. The medical image data can be cardiac image data acquired using any type of medical imaging modality, such as computed tomography (CT), three-dimensional rotational angiography, magnetic resonance imaging (MRI), ultrasound (US), etc., provided that the heart is visible in the medical image data. In an advantageous implementation, the medical image data includes three dimensional (3D) medical image data. The medical image data can be received directly from an image acquisition device, such as a CT scanner, a C-arm image-acquisition device, an MRI scanner, or an US scanner, or the medical image data can be received by loading previously stored cardiac image data of the patient. The medical image data may be pre-operative medical image data acquired prior to a cardiac EP intervention or intra-operative medical image data acquired during a cardiac EP intervention.

The BSP measurements of the patient are non-invasive measurements of potentials at particular points on the surface of the patient's body over time. In particular, the BSP measurements can be measurements of potentials at points on the patient's torso. The BSP measurements of the patient can be pre-operative or intra-operative. The use of pre-operative BSP measurements allows a patient-specific cardiac EP model to be generated and virtual electrophysiological interventions to be performed for pre-operative planning independent of any actual intervention procedure being performed. The use of intra-operative BSP measurements allows a patient-specific cardiac EP model to be generated and virtual electrophysiological interventions to be performed to guide an electrophysiological intervention in real-time or near real-time. In advantageous embodiments, the BSP measurements can be ECG measurements (12 lead, standard, etc.) of the patient or an electrocardiographic body surface mapping (BSM) of the patient.

At step 104, a patient-specific anatomical heart model is generated from the medical image data of the patient. In order to generate the patient-specific anatomical heart model, a patient-specific heart morphology model is extracted from the medical image data. The patient-specific heart morphology model can be a comprehensive geometrical model that represents the patient-specific heart morphology. In an advantageous embodiment, the patient-specific heart morphology model includes individual anatomical models representing the morphology of various heart components. The models are highly modular and can be customized depending on the application. The complete heart model can comprise the left ventricle (LV), left atrium (LA), left outflow tract, aortic root, pulmonary veins, right ventricle (RV), right atrium (RA), right outflow tract, RV neck, and veins. Papillaries and trabeculae can also be obtained, from CT images for instance. Each of these components can be used individually or jointly according to data availability and clinical application. In an exemplary embodiment, the LV and RV anatomical models estimated from the medical image data are used. In a possible implementation, only the LV and RV are explicitly modeled. In another possible implementation, models for all of the heart chambers are extracted. It is also possible that the comprehensive model including all of the heart components is extracted. The modularity of this framework enables using images in which only part of the anatomy is visible.

The anatomical model for each heart component can be extracted individually. In particular, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

The patient-specific heart morphology model is fused into a single volumetric mesh representation and surface elements of the mesh are tagged into surface zones. For example, in the case of VT/VF ablation therapy, the patient-specific LV and RV anatomical models can be fused into a single anatomical model of the bi-ventricular myocardium. In particular, the LV and RV anatomies are fused into a single volumetric mesh representation. The LV and RV models can be fused into a single volumetric mesh representation, on which vertices are tagged into surface zones (LV endocardium, LV septum, RV endocardium, RV septum) according to the underlying anatomy of the estimated surface models. According to an advantageous embodiment, tetrahedral elements can be used to accurately represent the details of the bi-ventricular anatomy. Spatial information, such as scars, grey zones, and fibrosis can be identified in images, such as late enhancement MRI. For example, the spatial information may be automatically identified using trained classifiers or may be manually identified by a clinician. The spatial information is mapped onto the tetrahedral mesh representing the bi-ventricular myocardium. This information is important to simulate the electrical wave around scars, in particular for wave-reentry assessment and correctly capture impaired cardiac mechanics due to ill-functioning or dead cells.

A model of fiber orientation can be automatically calculated based on the patient-specific geometry. In an advantageous implementation, the model of fiber orientation can be automatically calculated using a rule-based approach. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, e.g., from −70 on the epicardium to +70 on the endocardium (values that can be defined by the user). Similarly, the sheet direction, which is defined by the angle $\beta$ with respect to the outward transmural axis, varies transmurally, e.g., from +45 on the epicardium to −45 on the endocardium (values that can be defined by the user). $\alpha$ and $\beta$ are computed for each point of the volumetric bi-ventricular myocardium mesh between the apex and basal plane based on the geodesic distance to the endocardia and epicardia identified by the facet tags: $\alpha=(d_{epi}\alpha_{endo}+d_{endo}\alpha_{epi})/(d_{endo}+d_{epi})$, where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. In another embodiment, when MRI diffusion tensor imaging (DTI) is available, the fibers can be directly measured in-vivo, in the patient, using the MRI diffusion tensor imaging. In another embodiment, an atlas of cardiac fibers could be employed to register the fibers to the anatomical model. Additional details regarding generating the patient-specific anatomical heart model are described in U.S. Published Patent Application No. 2013/0197881 and U.S. Published Patent Application No. 2015/0042464, which are incorporated herein in their entirety by reference.

Figure 2:
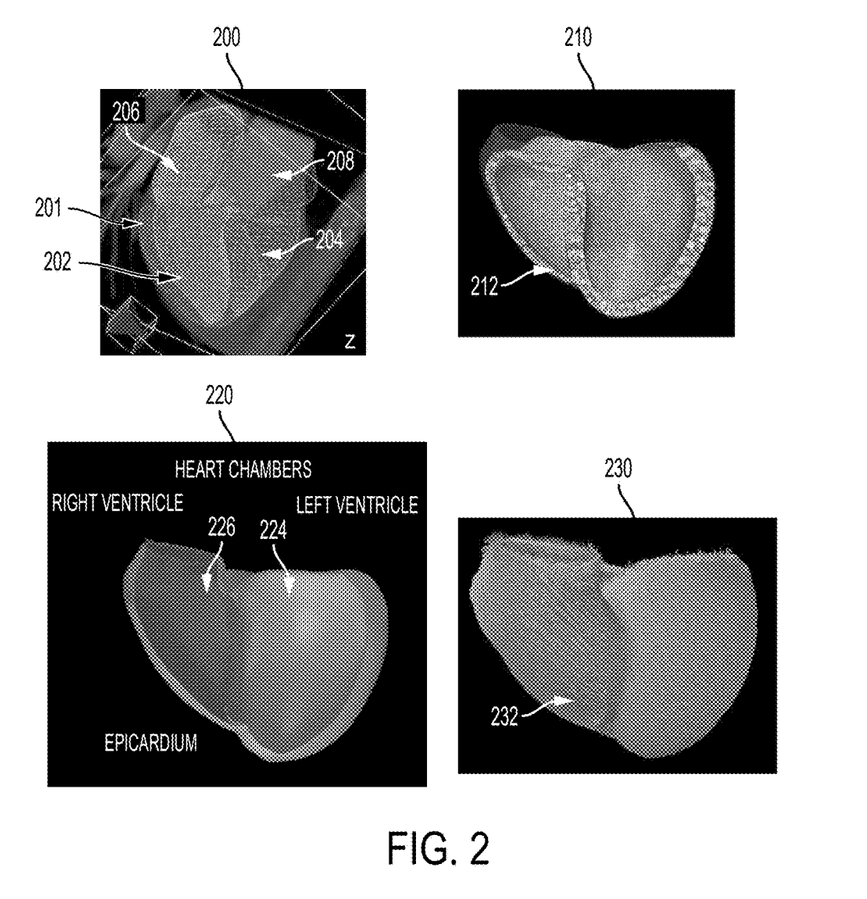
FIG. 2 illustrates exemplary results for generating a patient-specific anatomical heart model.

FIG. 2 illustrates exemplary results for generating a patient-specific anatomical heart model. As illustrated in FIG. 2, image 200 shows patient-specific anatomical models of the left ventricle epicardium 201, left ventricle endocardium 202, right ventricle 204, left atrium 206, and right atrium 208, automatically extracted from 3D CT image data. Image 210 shows a fused volumetric anatomical mesh 212 resulting from fusing the left ventricle epicardium, left ventricle endocardium, and right ventricle anatomical models. Image 220 shows exemplary results of automatic mesh tagging of the volumetric mesh. In particular, surface elements of the volumetric mesh in image 220 are tagged into surface zones of epicardium 222, left ventricle 224, and right ventricle 226. Image 230 shows exemplary results of generating the patient-specific model of the ventricular myocardium fiber architecture 232.

In addition to the patient-specific anatomical heart model, a detailed torso surface model of the patient can be extracted from the medical image data. For example, the detailed torso surface model can be extracted by automatically segmenting the patient's torso geometry from the medical image data using machine learning segmentation techniques.

Returning to FIG. 1, at step 106, a patient-specific computational cardiac electrophysiology (EP) model is generated based on the patient-specific anatomical heart model and the body surface potential measurements of the patient. The patient-specific cardiac EP model is a computational model of cardiac electrophysiology and potential propagation throughout the torso, the parameters of which are estimated based on a comparison of torso potentials simulated using the cardiac EP model and the BSP measurements of the patient in order to personalize the patient-specific cardiac EP model for the patient.

Figure 3:
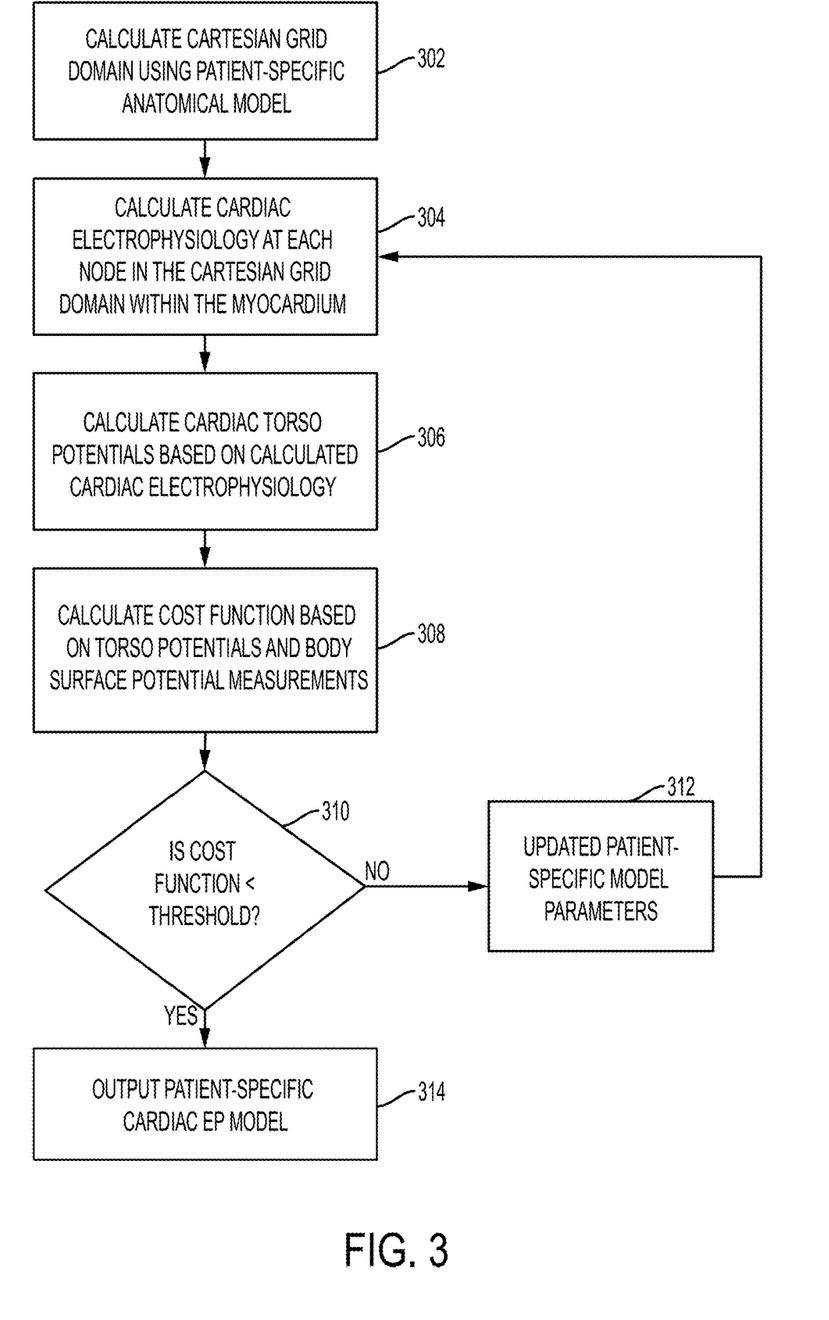
FIG. 3 illustrates a method for generating a patient-specific computational model of cardiac electrophysiology according to an embodiment of the present invention.

FIG. 3 illustrates a method for generating a patient-specific computational model of cardiac electrophysiology according to an embodiment of the present invention. The method of FIG. 3 can be used to implement step 106 of FIG. 1. Referring to FIG. 3, at step 302, a Cartesian grid domain for electrophysiology computations is calculated using the patient-specific anatomical heart model. A Cartesian grid, possibly with unequal and spatially varying spacing, is first generated in a bounding box surrounding the anatomical heart model. Grid spacing can be defined by the user or fixed in the system. A level-set representation is then calculated from the patient-specific anatomical mesh as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as septal nodes. Available scars and border zones are also reported in the domain through additional level-set information. Fiber orientation f(x) are mapped to each node using rasterization techniques or recomputed from the mapped endocardial and epicardial zones. A diffusion coefficient D(x) and an action potential duration APD(x) is assigned to every myocardial node x of the Cartesian grid. Cell model parameters can also be mapped spatially at each node.

At step 304, cardiac electrophysiology is calculated at each node of the Cartesian grid domain within the myocardium using a computational model of cardiac electrophysiology. According to an advantageous embodiment of the present invention, cardiac electrophysiology is calculated at each node within the myocardium using the Lattice-Boltzmann Method for Electrophysiology (LBM-EP) to solve a cardiac electrophysiology model at each node. The cardiac electrophysiology model calculates the variation of the transmembrane potential v(x,t) over time according to the mono-domain equation:

$$\frac{dv(x,t)}{dt} = R(x,t) + \nabla \cdot D(x)K(x)\nabla v(x,t), \quad (1)$$

where R(x,t) is a reaction term describing the cellular mechanisms giving rise to the action potential, D(x) is the local diffusivity to be estimated from the patient-specific data, K(x) is the anisotropy matrix defined by $(1-\rho)f(x)f(x)^T+\rho I d$, $\rho$ being the ratio between the cross-fiber diffusivity and the fiber diffusivity (typically $\rho=0.11-0.25$). It is also possible to use orthotropic or fully anisotropic tensors K(x) for improved characterization of the fiber architecture.

The choice of the reaction term R(x,t) depends on the cellular model of cardiac electrophysiology that is used. The method disclosed herein is modular in that it can handle any standard mono-domain models, such as, but not limited to the "Mitchell-Schaeffer model" proposed in Mitchell et al., "A Two-Current Model for the Dynamics of Cardiac Membrane", *Bulletin of Mathematical Biology*, 65(5):767-793, 2003, or the model proposed in Ten Tusscher, et al., "Cell Model for Efficient Simulation of Wave Propagation in Human Ventricular Tissue Under Normal and Pathological Conditions", *Physics in Medicine and Biology*, 51, pp 6141, 2006. For the Mitchell-Schaeffer model for instance, we have:

$$R(x,t) = \frac{h(x,t)v^2(x,t)(1-v(x,t))}{\tau_{in}} - \frac{v(x,t)}{\tau_{out}} + J_{stim}(x). \quad (2)$$

In this equation $J_{stim}(x)$ is an external stimulus current. In intraoperative intervention planning, when the electrophysiologist is pacing the heart at a given location, the position of the pacing catheter is tracked using an embedded tracking method (e.g., electromagnetic tracking, bi-plane image-based tracking, etc.), and the position of the pacing catheter returned by the embedded tracking method is used to add a stimulus current to the model through $J_{stim}(x)$ at the acquired position. Virtual pacing is achieved by adding $J_{stim}(x)$ at a spatial location chosen by the user or chosen automatically by the system. The amount of current that is added to the model is obtained from the catheter manufacturer specifications.

In Equation (2), h(x,t) is a gating variable that controls the state of the ion channels according to the following ordinary differential equation:

$$\frac{dh(x,t)}{dt} = \begin{cases} \dfrac{1-h(x,t)}{\tau_{open}} & \text{if } v(x,t) < v_{gate} \\ \dfrac{-h(x,t)}{\tau_{close}} & \text{otherwise} \end{cases}$$

$v_{gate}$ is a potential threshold, and $T_{in}$, $T_{out}$, $T_{open}$ and $T_{close}$ are parameters controlling the shape of the action potential. FIG. 9 illustrates relationships between model parameters and the shape of the action potential for the Mitchell-Schaeffer model. As shown in FIG. 9, the maximum action potential duration APD(x) is directly related to $T_{close}(x)$ according to the formula $APD_{max}(x)=T_{close}(x)\ln(T_{out}/(4T_{in}))$. In an advantageous embodiment of the present invention, only D(x) and $T_{close}(x)$ are estimated, the other parameters are kept constant to their default (i.e. nominal) values. However, it is also possible to implement this method to estimate these additional parameters as well.

Equation (1) is solved using the Lattice-Boltzmann method, referred to herein as LBM-EP. LBM-EP is a highly parallelizable algorithm to solve mono-domain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In the method of FIG. 7, domain boundaries are represented as level-sets and tissue anisotropy is modeled. Since the method is node-wise, the algorithm is highly parallelizable. In an advantageous embodiment, the method can be implemented on a graphics processing unit (GPU), which enables near real-time and accurate cardiac electrophysiology computation during an intervention. In sinus rhythm, the electrocardiography model is computed with periodic stimulus at the septum to mimic the effects of the His bundle. The electrocardiography model can be initialized with high diffusivity coefficients on the endocardia to mimic the effect of Purkinje fibers, and lower diffusivity throughout the myocardium. These initial values are then updated in one or more subsequent iterations based on the patient-specific measurements received during the intervention to fit the cardiac electrocardiography model to the patient-specific measurements. It should be noted that since the framework relies on Cartesian grids, it is relatively simple to add more structural information in the model. For instance, Purkinje fibers, if available, can be added directly into the domain through rasterization. The His bundle and other electrophysiology bundles can be integrated similarly.

In an advantageous implementation, the outputs of calculating the cardiac electrophysiology at each node in the Cartesian grid domain within the myocardium at step 304 are i) a time varying 3D potential map; ii) a 3D map of depolarization times $t_{dep}(x)|v(x,t_{dep}-dt)<V_{gate}$, $v(x,t_{dep})>V_{gate}$; and a 3D map of repolarization times $t_{rep}(x)|V(x,t_{dep}-dt)>V_{gate}$, $v(x,t_{dep})<V_{gate}$. Additionally, other guidance maps, such as a 3D map of tissue diffusivity D(x) and a 3D map of action potential duration APD(x), can also be generated in step 304.

At step 306, torso potentials are calculated based on the cardiac electrophysiology calculated in step 304. In step 304, the transmembrane potential v(x,t) at each node within the myocardium is calculated. Once the transmembrane potential v(x,t) is calculated, the extra-cellular potential $\Phi_e$ at each node can be calculated using a closed-form expression ($\Omega$ defines the computational domain; $|\Omega|$ is the number of elements therein):

$$\phi_e(x, t) = \frac{\lambda}{1+\lambda} \frac{1}{|\Omega|} \int_\Omega [v(y, t) - v(x, t)] dy$$

where $\lambda$ is a constant diffusion anisotropy ratio, $\lambda = D_i(x)/D_e(x)$, and $D_i$ and $D_e$ are intra- and extra-cellular diffusivity tensors. The extra-cellular potential $\phi_e$ is then mapped back to the epicardium surface mesh using tri-linear interpolation. The extra-cellular potentials are then projected onto the torso surface using a boundary element method (BEM). The potential $\phi(x)$ at any point x of the thoracic domain can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[ \phi_e \frac{r \cdot n}{\|r\|^3} + \frac{\nabla \phi_e \cdot n}{\|r\|} \right] dS_H$$

where r is the vector defined by x and the integration point, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. As described above, a torso mesh can be segmented from the medical image data using machine learning algorithms. According to a possible implementation, the body surface potential $\phi_b$ can be calculated for each vertex on the torso mesh. In another possible implementation, the body surface potential $\phi_b$ may be calculated only for vertices on the torso mesh corresponding to lead locations of leads used to acquire the BSP measurements (e.g., ECG or BSM) of the patient.

At step 308, a cost function is calculated based on the calculated torso potentials and the BSP measurements of the patient. The cost function is a measure of error between the simulated torso potentials calculated in step 306 and the measured torso potentials in the BSP measurements of the patient. According to an advantageous implementation, the cost function may be a mean squared difference between the computed and measured torso potentials at each of the lead locations used to acquire the measured torso potentials. At step 310, it is determined if the cost function is less than a threshold. If the cost function is greater than the threshold, the method proceeds step 312. If the cost function is less than the threshold, the method proceeds step 314.

At step 312, when the cost function is greater than the threshold, the patient-specific model parameters of the cardiac electrophysiology model are updated based on the BSP measurements of the patient. In particular, an inverse problem algorithm can be utilized to automatically estimate the diffusivity D(x) and action potential duration APD(x) parameters of the cardiac electrophysiology model based on the BSP measurements of the patient. The aim of the inverse problem algorithm is to determine D(x) and APD(x) that minimize the cost function. In an advantageous embodiment, a gradient free optimization algorithm, such as NEWUOA, can be used to perform the iterative optimization of the cardiac EP model parameters. A multi-level, hierarchical, coarse-to-fine approach can be utilized to estimate the spatially varying electrical conductivity (diffusivity) and action potential parameters. In another possible implementation, the diffusivity coefficient can be sub-divided according to the American Heart Association (AHA) 17 segment guidelines, with the diffusivity for each segment considered to be constant. This reduces the number of parameters to be optimized to 17. When available, scare and tissue imaging can be used in predefined regions of interest with significantly different parameters, like scars and border zones. This prior knowledge further increases computational efficiency and method accuracy. According to a possible embodiment, an estimate of local parameter uncertainty can be calculated by performing a sensitivity analysis with cost function variations, which is made possible by the efficient EP model utilized for simulating cardiac EP.

Once the patient-specific parameters D(x) and APD(x) of the cardiac electrophysiology model are updated, the method returns to step 304 and repeats 304, 306, 308, 310, and 312 until the cost function is less than the threshold, indicating that the torso potentials calculated using the cardiac electrophysiology model is sufficiently fit to the BSP measurements of the patient. This results in the patient-specific cardiac EP model for the patient.

At step 314, when the cost function is less than the threshold, the patient-specific cardiac EP model is output. In particular, the patient-specific parameters for the cardiac EP model are set and the patient-specific cardiac EP model can be used for patient-specific electrophysiology simulations. The patient-specific tissue parameters of the cardiac EP model can also be output, for example, by displaying a 3D map of tissue diffusivity and a 3D map of action potential duration on a display of a computer system.

Figure 4:
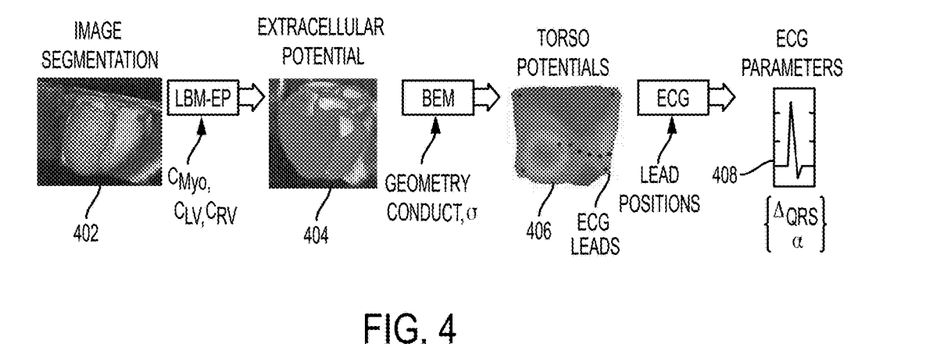
FIG. 4 illustrates an example of forward modeling of the generation of body surface potentials and ECG signals from medical images of the patient's anatomy according to an embodiment of the present invention.

Returning to FIG. 1, at step 108, cardiac electrophysiology, extracellular potentials, and torso potentials are simulated using the patient-specific cardiac EP model. In particular, transmembrane potentials are simulated at each node of the myocardium using the patient-specific cardiac EP model as described in connection with step 304 of FIG. 3. Extracellular potentials are calculated based on the simulated and transmembrane potentials and torso potentials are calculated using the extracellular potentials as described in connection with step 306 of FIG. 3. Furthermore, a simulated ECG signal can be calculated based on the simulated torso potentials. In particular, the simulated ECG signal is generated using the simulated torso potentials at the locations of the standard ECG leads. FIG. 4 illustrates an example of forward modeling of the generation of body surface potentials and ECG signals from medical images of the patient's anatomy according to an embodiment of the present invention. As shown in image 402 of FIG. 4, medical image data of the patient is segmented to generate a patient-specific anatomical heart model. The patient-specific anatomical heart model provides a computational domain for solving a patient-specific electrophysiology model using the Lattice-Boltzmann method for electrophysiology (LBM-EP), which is personalized by estimating patient-specific parameters for the diffusion coefficient and action potential duration. As shown in image 404, extra-cellular potentials are estimated from trans-membrane potentials calculated by the patient-specific EP model. As shown in image 406, the extra-cellular potentials are projected onto the torso using a boundary element method (BEM) and ECG leads are derived. As shown in image 408, an ECG signal is calculated from the torso potentials at the ECG leads positions and ECG parameters are visualized.

Intervention planning can be performed by simulating different virtual interventions using the patient-specific cardiac EP model. Since the system is generative, cardiac electrophysiology can be computed under different virtual interventions. As a result, several therapeutic scenarios can be tested in-silico. The virtual electrophysiological interventions can be used for pre-operative planning or intra-operative guidance. For each virtual electrophysiological intervention, the transmembrane potentials, extra-cellular potentials, torso potentials, and simulated ECG signal can be simulated. In order to perform a virtual intervention, a virtual pacing catheter location can be received. Since the system is generative, the user (e.g., physician) can select one or more locations to virtually pace the heart, given the current estimate of the diffusivity map $D(x)$ and the action potential duration map $APD(x)$. The user can input a spatial location for a virtual pacing catheter, for example using an input device, such as a mouse, touch screen, etc., of a computer system to select a spatial location on the anatomical heart model or one of the cardiac electrocardiography maps generated by the patient-specific cardiac EP model. In an alternative implementation, systematic virtual pacing may be automatically applied by rasterizing the model, in order to detect optimal pacing locations. In particular, a sampling scheme can be used to automatically select virtual pacing locations, and a virtual electrophysiological intervention can be performed for each pacing location. The cardiac electrophysiology is then calculated using the patient-specific cardiac EP model. In particular, a current $J_{stim}$ is added to the patient-specific cardiac EP model at the location of the virtual pacing catheter and the cardiac electrophysiology, including the transmembrane potentials, extra-cellular potentials, and torso potentials, is computed over a period of time. The system allows for virtual ablation by locally setting the tissue diffusivity to 0 to mimic the ablated lesion.

Returning to FIG. 1, at step 110, the simulation results are output. For example, dynamic electrophysiology maps (e.g., dynamic potential maps) can be visualized on the epicardium, endocardium, the whole myocardium volume, any layer within the myocardium, the torso, or anywhere else in the volume, and these maps can be displayed on a display device. In addition, 3D maps for spatially varying entities, such as TMP, electrical conductivity (diffusion parameters), and action potential parameters (e.g., action potential duration) can be visualized and displayed. For example, the spatially varying entities can be visualized by color coding the mesh of the patient's anatomy. Other electrophysiological maps, such as a 3D map of depolarization times, and a 3D map of repolarization times, can also be visualized and displayed. Uncertainty calculated for the estimated myocardium electrical conductivity and action potential parameters can be also be visualized. Myocardium diffusivity maps can be reconstructed and visualized with variable spatial resolutions.

As described above, non-invasive BSP measurements are used to optimize patient-specific parameters for the cardiac EP model. According to another possible embodiment, the optimization framework can be further constrained if endocardial EP measurements are available. Assuming that endocardial mapping is performed as well as body surface mapping, the cost function used in the optimization procedure can minimize the difference between the simulated myocardium and body surface potentials and the endocardial EP measurements and the BSP measurements. Although, in this case, the assessment is still invasive, combining both endocardial and surface mapping measurements will enable the user to get endocardial samples at a very few locations.

Because the approach described herein relies on a forward model of cardiac electrophysiology, it can be extended by including cardiac biomechanics, and therefore cope with the effect of cardiac motion on the body surface potentials. For example, in one possible embodiment, a moving mesh can be automatically estimated from 4D thoracic images and cardiac EP is solved on the moving mesh to cope with myocardium deformations. In another possible embodiment, cardiac biomechanics can be directly computed using a biomechanical model of myocardium tissue, where the model is controlled by estimated cardiac parameters.

In the embodiment described above, a tetrahedral mesh is utilized to calculate the anatomical model. In an alternative implementation, the anatomical model can be computed directly on the computational grid.

In the embodiment described above, a direct optimization technique is utilized. It is to be understood that other inverse problem methods can also be used, such as Kalman filtering, simplex methods, and variational approached. Furthermore, data-driven approaches can also be employed due to the computational efficiency of the forward TMP and BSP model. A large database of simulated (BSP/EP parameters) vectors can be created, and a regression model from BSP to EP parameters can be estimated using non-linear or linear manifold learning. The regression model can then be used to predict the EP parameters given the BSP of a patient, and the EP parameters can then be used to derive the transmembrane potential dynamic maps for the patient.

Figure 5:
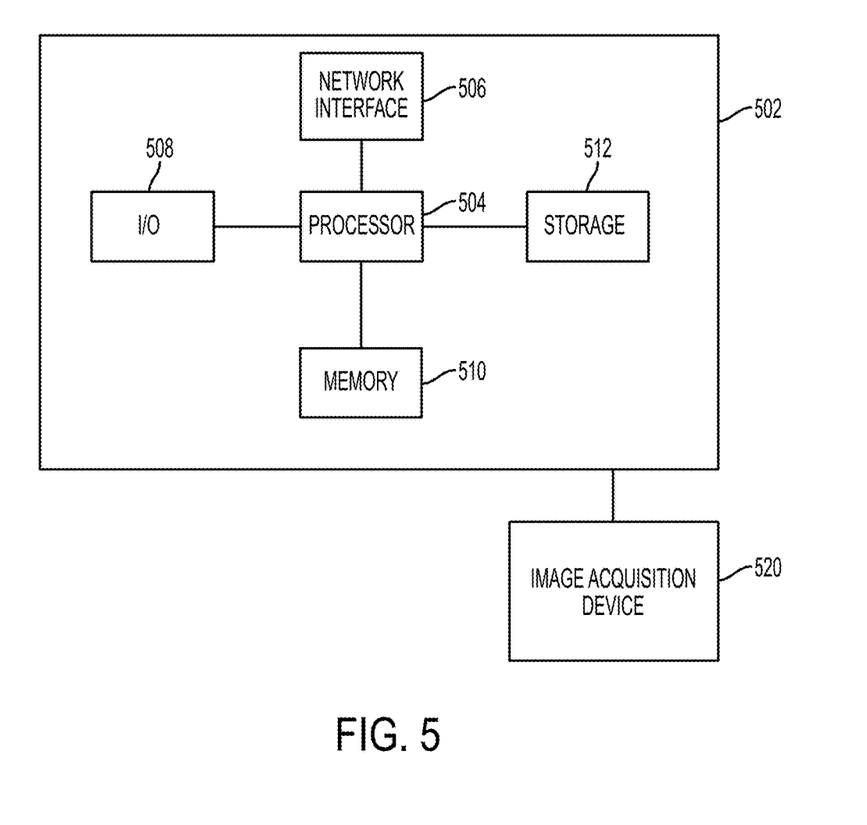
FIG. 5 is a high-level block diagram of a computer capable of implementing the present invention.

The above-described methods for patient-specific simulation of cardiac electrophysiology can be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the methods of FIGS. 1 and 3 may be defined by the computer program instructions stored in the memory 510 and/or storage 512 and controlled by the processor 504 executing the computer program instructions. An image acquisition device 520, such as a CT scanning device, C-arm image acquisition device, MR scanning device, Ultrasound device, etc., can be connected to the computer 502 to input image data to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for non-invasively simulating patient-specific cardiac electrophysiology, comprising:
    generating a patient-specific anatomical heart model from medical image data of a patient;
    computing torso potentials over time at locations on a torso of the patient using the patient-specific anatomical heart model, a patient-specific anatomical arrangement between the heart and torso, and a cardiac electrophysiology model with certain model parameters;
    estimating patient-specific model parameters of the cardiac electrophysiology model by refining the model parameters of the cardiac electrophysiology model to minimize an error between the computed torso potentials and body surface potential measurements acquired for the patient;
    simulating patient-specific electrophysiological measurements including transmembrane potentials in a myocardium of the patient-specific anatomical heart model, extra-cellular potentials, and torso potentials using the cardiac electrophysiology model with the patient-specific model parameters; and
    generating at least one of a visualization of the simulated patient-specific electrophysiological measurements or patient-specific electrophysiology parameter maps based on the patient-specific anatomical heart model, the patient-specific anatomical arrangement between the heart and torso, and the cardiac electrophysiology model with the patient-specific model parameters.

2. The method of claim 1, wherein computing torso potentials over time at locations on a torso of the patient using the patient-specific anatomical heart model, a patient-specific anatomical arrangement between the heart and torso, and a cardiac electrophysiology model with certain model parameters comprises:
    simulating transmembrane potentials over time in a myocardium of the patient-specific anatomical heart model using the cardiac electrophysiology model; and
    simulating the torso potentials over time based on the simulated transmembrane potentials in the myocardium.

3. The method of claim 2, wherein simulating transmembrane potentials over time in a myocardium of the patient-specific anatomical heart model using the cardiac electrophysiology model comprises:
    generating a Cartesian grid domain using the patient-specific anatomical heart model; and
    calculating transmembrane potential variation over time at each of a plurality of nodes within the myocardium in the Cartesian grid domain by computing a solution of the cardiac electrophysiology model for each of the plurality of nodes using a Lattice-Boltzmann method for electrophysiology.

4. The method of claim 2, wherein simulating the torso potentials over time based on the simulated transmembrane potentials in the myocardium comprises:
    calculating extra-cellular potentials based on the simulated transmembrane potentials in the myocardium; and
    calculating the simulated torso potentials at a plurality of points on the torso based on the extra-cellular potentials.

5. The method of claim 1, wherein estimating and refining the model parameters to minimize an error between the computed torso potentials and body surface potential measurements acquired for the patient comprises:
    calculating a cost function that compares the computed torso surface potentials with corresponding measured body surface potentials; and
    estimating the model parameters of the cardiac electrophysiology model to minimize the cost function.

6. The method of claim 1, wherein estimating patient-specific model parameters of the cardiac electrophysiology model by refining the model parameters of the cardiac electrophysiology model to minimize an error between the computed torso potentials and body surface potential measurements acquired for the patient comprises:
    calculating patient-specific electrical diffusivity and action potential duration parameters of the cardiac electrophysiology model to minimize the error between the computed torso surface potentials and the body surface potential measurements of the patient.

7. The method of claim 1, wherein the body surface potential measurements of the patient are ECG measurements of the patient, and computing torso potentials over time at locations on a torso of the patient using the patient-specific anatomical heart model, a patient-specific anatomical arrangement between the heart and torso, and a cardiac electrophysiology model with certain model parameters comprises:
    simulating transmembrane potentials over time in a myocardium of the patient-specific anatomical heart model using the cardiac electrophysiology model; and
    simulating ECG potentials over time at points on the torso corresponding positions of ECG leads used to acquire the ECG measurements based on the simulated transmembrane potentials in the myocardium.

8. The method of claim 7, wherein estimating patient-specific model parameters of the cardiac electrophysiology model by refining the model parameters of the cardiac electrophysiology model to minimize an error between the computed torso potentials and body surface potential measurements acquired for the patient comprises:
    calculating patient-specific parameters of the cardiac electrophysiology model that minimize an error between the simulated ECG potentials and the ECG measurements at the points on the torso corresponding to the ECG leads.

9. The method of claim 1, wherein the body surface potential measurements of the patient are acquired using a body surface mapping of the patient, and computing torso potentials over time at locations on a torso of the patient using the patient-specific anatomical heart model, a patient-specific anatomical arrangement between the heart and torso, and a cardiac electrophysiology model with certain model parameters comprises:

simulating transmembrane potentials over time in a myocardium of the patient-specific anatomical heart model using the cardiac electrophysiology model; and simulating the torso potentials over time at points on the torso corresponding positions of leads used to acquire the body surface mapping of the patient based on the simulated transmembrane potentials in the myocardium.

10. The method of claim 9, wherein estimating and refining the model parameters to minimize an error between the computed torso potentials and body surface potential measurements acquired for the patient comprises:

calculating patient-specific parameters of the cardiac electrophysiology model that minimize an error between the simulated torso potentials and the body surface potential measurements at the points on the torso corresponding to the leads used to acquire the body surface mapping of the patient.

11. The method of claim 1, wherein simulating patient-specific electrophysiological measurements including transmembrane potentials in a myocardium of the patient-specific anatomical heart model, extra-cellular potentials, and torso potentials using the cardiac electrophysiology model with the patient-specific model parameters comprises:

simulating transmembrane potentials over time in a myocardium of the patient-specific anatomical heart model using the cardiac electrophysiology model with the patient-specific model parameters;

simulating extra-cellular potentials over time based on the simulated transmembrane potentials in the myocardium; and simulating torso potentials at a plurality of points on the torso based on the extra-cellular potentials.

12. The method of claim 11, wherein the plurality of points on the torso are ECG lead locations, and simulating patient-specific electrophysiological measurements including transmembrane potentials in a myocardium of the patient-specific anatomical heart model, extra-cellular potentials, and torso potentials using the cardiac electrophysiology model with the patient-specific model parameters further comprises:

simulating an ECG signal based on the simulated torso potentials at the ECG lead locations.

13. The method of claim 11, wherein generating at least one of a visualization of the simulated patient-specific electrophysiological measurements or patient-specific electrophysiology parameter maps based on the patient-specific anatomical heart model, the patient-specific anatomical arrangement between the heart and torso, and the cardiac electrophysiology model with the patient-specific model parameters comprises:

generating dynamic potential maps of the transmembrane potentials in the myocardium, the extra-cellular potentials, and the torso potentials.

14. The method of claim 1, wherein generating at least one of a visualization of patient-specific electrophysiological measurements or patient-specific electrophysiology maps based on the patient-specific anatomical heart model, the patient-specific anatomical arrangement between the heart and torso, and the cardiac electrophysiology model with refined model parameters comprises:

generating one or more of a dynamic potential map of the epicardium, a dynamic potential map of the endocardium, or a dynamic potential map of at least one layer of the myocardium.

15. The method of claim 1, wherein generating at least one of a visualization of patient-specific electrophysiological measurements or patient-specific electrophysiology maps based on the patient-specific anatomical heart model, the patient-specific anatomical arrangement between the heart and torso, and the cardiac electrophysiology model with refined model parameters comprises:

generating at least one of a 3D map of personalized electrical diffusivity values of the patient-specific cardiac electrophysiology model or a 3D map of personalized action potential duration values of the patient-specific cardiac electrophysiology model.

16. The method of claim 1, wherein generating at least one of a visualization of patient-specific electrophysiological measurements or patient-specific electrophysiology maps based on the patient-specific anatomical heart model, the patient-specific anatomical arrangement between the heart and torso, and the cardiac electrophysiology model with refined model parameters comprises:

receiving a user input selecting a spatial location and pacing protocols of a virtual pacing catheter;

simulating the cardiac electrophysiology over time using the cardiac electrophysiology model with the refined parameters with a stimulus current added at the spatial location of the virtual pacing catheter; and generating patient-specific electrophysiology maps based on the simulated cardiac electrophysiology using the cardiac electrophysiology model with the refined parameters with a stimulus current added at the spatial location of the virtual pacing catheter.

\* \* \* \* \*